(12) United States Patent
Paquet et al.

(10) Patent No.: US 11,083,415 B2
(45) Date of Patent: Aug. 10, 2021

(54) VITAL-SIGNS PATCH HAVING A STRAIN RELIEF

(71) Applicant: CareFusion 303, Inc., San Diego, CA (US)

(72) Inventors: Pierre Paquet, Quebec (CA); Mark Raptis, Valley Center, CA (US)

(73) Assignee: CAREFUSION 303, INC., San Diego, CA (US)

( * ) Notice: Subject to any disclaimer, the term of this patent is extended or adjusted under 35 U.S.C. 154(b) by 682 days.

(21) Appl. No.: 15/426,009

(22) Filed: Feb. 6, 2017

(65) Prior Publication Data

US 2017/0143264 A1 May 25, 2017

Related U.S. Application Data

(62) Division of application No. 12/844,774, filed on Jul. 27, 2010, now Pat. No. 9,585,620.

(51) Int. Cl.
| | |
|---|---|
| *A61B 5/282* | (2021.01) |
| *A61B 5/00* | (2006.01) |
| *A61B 5/145* | (2006.01) |
| *G16H 40/67* | (2018.01) |
| *A61B 5/0205* | (2006.01) |

(Continued)

(52) U.S. Cl.
CPC .......... *A61B 5/6833* (2013.01); *A61B 5/0022* (2013.01); *A61B 5/02055* (2013.01); *A61B 5/1477* (2013.01); *A61B 5/14542* (2013.01); *A61B 5/282* (2021.01); *A61B 5/6813* (2013.01); *G16H 40/67* (2018.01); *A61B 5/01* (2013.01); *A61B 5/02* (2013.01); *A61B 5/021* (2013.01); *A61B 5/024* (2013.01); *A61B 5/0816* (2013.01); *A61B 5/6823* (2013.01); *A61B 2562/164* (2013.01)

(58) Field of Classification Search
CPC .... A61B 5/6833; A61B 5/02055; A61B 5/282
See application file for complete search history.

(56) References Cited

U.S. PATENT DOCUMENTS

| | | | |
|---|---|---|---|
| 3,677,261 A | 7/1972 | Day | |
| 3,805,769 A | 4/1974 | Sessions | |

(Continued)

FOREIGN PATENT DOCUMENTS

| | | |
|---|---|---|
| EP | 1748289 A2 | 1/2007 |
| JP | 61003019 | 1/1986 |

(Continued)

OTHER PUBLICATIONS

W. J. Tompkins, Biomedical Digital Signal Processing. Prentice Hall, New Jersey, 1993; p. 1-378 (Year:1993).

(Continued)

*Primary Examiner* — John R Downey
(74) *Attorney, Agent, or Firm* — Morgan, Lewis & Bockius LLP

(57) ABSTRACT

A vital-signs monitor patch containing at least two electrodes, a circuit assembly, and a patch body having a chamber in which the circuit assembly is housed. The patch body also contains at least one flexible portion adjacent to the circuit assembly chamber, with at least one electrode attached to the flexible portion. The electrodes are configured for attaching the patch to the skin of a patient.

20 Claims, 8 Drawing Sheets

(51) Int. Cl.
   *A61B 5/1477*   (2006.01)
   *A61B 5/01*     (2006.01)
   *A61B 5/02*     (2006.01)
   *A61B 5/08*     (2006.01)
   *A61B 5/021*    (2006.01)
   *A61B 5/024*    (2006.01)

(56) References Cited

U.S. PATENT DOCUMENTS

| | | |
|---|---|---|
| 3,830,224 A | 8/1974 | Vanzetti et al. |
| 3,845,757 A | 11/1974 | Weyer |
| 4,121,574 A | 10/1978 | Lester |
| 4,396,020 A | 8/1983 | Wolff et al. |
| 4,407,295 A | 10/1983 | Steuer et al. |
| 4,490,005 A | 12/1984 | Hovey |
| 4,527,087 A | 7/1985 | Taya et al. |
| 4,530,366 A | 7/1985 | Nessi et al. |
| 4,539,996 A | 9/1985 | Engel |
| 4,541,734 A | 9/1985 | Ishizaka |
| 4,554,924 A | 11/1985 | Engel |
| 4,640,289 A | 2/1987 | Craighead |
| 4,686,998 A | 8/1987 | Robbins |
| 4,708,146 A | 11/1987 | Lane |
| 4,715,382 A | 12/1987 | Strand |
| 4,765,340 A | 8/1988 | Sakai et al. |
| 4,771,713 A | 9/1988 | Kinzenbaw |
| 4,838,273 A | 6/1989 | Cartmell |
| 4,846,185 A | 7/1989 | Carim |
| 4,848,353 A | 7/1989 | Engel |
| 4,967,765 A | 11/1990 | Turner et al. |
| 5,012,810 A | 5/1991 | Strand et al. |
| 5,050,612 A | 9/1991 | Matsumura |
| 5,094,545 A | 3/1992 | Larsson et al. |
| 5,133,356 A | 7/1992 | Bryan et al. |
| 5,153,584 A | 10/1992 | Engira |
| 5,215,087 A | 6/1993 | Anderson et al. |
| 5,258,577 A | 11/1993 | Clements |
| 5,273,036 A | 12/1993 | Kronberg et al. |
| 5,285,577 A | 2/1994 | Carney et al. |
| 5,344,335 A | 9/1994 | Scholz et al. |
| 5,353,793 A | 10/1994 | Bornn |
| 5,401,100 A | 3/1995 | Thackston et al. |
| 5,511,553 A | 4/1996 | Segalowitz |
| 5,544,661 A | 8/1996 | Davis et al. |
| 5,634,468 A | 6/1997 | Platt et al. |
| 5,803,915 A | 9/1998 | Kremenchugsky et al. |
| 5,971,930 A | 10/1999 | Elghazzawi |
| 5,980,467 A | 11/1999 | Henry |
| 6,030,342 A | 2/2000 | Amano et al. |
| 6,042,966 A | 3/2000 | Cheu |
| 6,090,050 A | 7/2000 | Constantinides |
| 6,222,456 B1 | 4/2001 | Tice |
| 6,270,252 B1 | 8/2001 | Siefert |
| 6,273,886 B1 | 8/2001 | Edwards et al. |
| 6,287,252 B1 | 9/2001 | Lugo |
| 6,324,426 B1 | 11/2001 | Thompson |
| 6,355,031 B1 | 3/2002 | Edwards et al. |
| 6,358,245 B1 | 3/2002 | Edwards et al. |
| 6,416,471 B1 | 7/2002 | Kumar et al. |
| 6,453,186 B1 * | 9/2002 | Lovejoy ............... A61B 5/282 600/386 |
| 6,454,708 B1 * | 9/2002 | Ferguson ............ A61B 5/6831 600/300 |
| 6,468,261 B1 | 10/2002 | Small et al. |
| 6,472,612 B2 * | 10/2002 | Fartash ................ G01K 7/04 174/260 |
| 6,472,614 B1 | 10/2002 | Dupont et al. |
| 6,494,829 B1 | 12/2002 | New, Jr. et al. |
| 6,665,802 B1 | 1/2003 | Ober |
| 6,517,497 B2 | 2/2003 | Rymut et al. |
| 6,636,754 B1 | 10/2003 | Baura et al. |
| 6,719,701 B2 | 4/2004 | Lade |
| 6,740,049 B2 | 5/2004 | Wallach |
| 6,740,059 B2 | 5/2004 | Flaherty |
| 6,950,688 B2 | 9/2005 | Axelgaard et al. |
| 6,963,772 B2 | 11/2005 | Bloom et al. |
| 6,980,112 B2 | 12/2005 | Nee |
| 7,052,472 B1 | 5/2006 | Miller et al. |
| 7,061,858 B1 | 6/2006 | Di Benedetto et al. |
| 7,198,600 B2 | 4/2007 | Tamaki et al. |
| 7,206,630 B1 * | 4/2007 | Tarler ................... A61B 5/6833 600/509 |
| 7,215,989 B1 * | 5/2007 | Burks ................... A61B 5/282 600/393 |
| 7,319,895 B2 | 1/2008 | Klefstad-Sillonville et al. |
| 7,355,512 B1 | 4/2008 | Al-Ali |
| RE40,470 E | 8/2008 | Fitzpatrick et al. |
| 7,434,991 B2 | 10/2008 | Harr et al. |
| 7,447,526 B2 | 11/2008 | Kim et al. |
| 7,538,682 B2 | 5/2009 | Trost et al. |
| 7,542,437 B1 | 6/2009 | Redi et al. |
| 7,639,352 B2 | 12/2009 | Huber et al. |
| 7,639,652 B1 | 12/2009 | Amis et al. |
| 7,645,263 B2 | 1/2010 | Angel et al. |
| 7,668,588 B2 | 2/2010 | Kovacs |
| 7,924,150 B2 | 4/2011 | Baldus et al. |
| 7,959,574 B2 | 6/2011 | Bardy |
| 7,962,188 B2 | 6/2011 | Kiani et al. |
| 8,007,436 B2 | 8/2011 | Katayama |
| 8,200,320 B2 | 6/2012 | Kovacs |
| 8,226,572 B2 | 7/2012 | Keith et al. |
| 8,228,188 B2 | 7/2012 | Key et al. |
| 8,231,542 B2 | 7/2012 | Keith et al. |
| 8,496,597 B2 | 7/2013 | James et al. |
| 8,506,480 B2 | 8/2013 | Banet et al. |
| 8,721,562 B2 | 5/2014 | Abreu |
| 9,055,925 B2 | 6/2015 | Paquet |
| 9,724,016 B1 | 8/2017 | Al-Ali |
| 10,285,617 B2 * | 5/2019 | Toth .................... A61B 5/282 |
| 2001/0027384 A1 | 10/2001 | Schulze |
| 2001/0047127 A1 | 11/2001 | New et al. |
| 2002/0007676 A1 | 1/2002 | Ward et al. |
| 2002/0013538 A1 | 1/2002 | Teller |
| 2002/0045836 A1 | 4/2002 | Alkawwas |
| 2002/0099277 A1 | 7/2002 | Harry et al. |
| 2002/0107436 A1 | 8/2002 | Barton et al. |
| 2002/0109621 A1 | 8/2002 | Khair et al. |
| 2002/0198519 A1 | 12/2002 | Qin et al. |
| 2003/0004403 A1 | 1/2003 | Drinan et al. |
| 2003/0028672 A1 | 2/2003 | Goldstein |
| 2003/0040305 A1 | 2/2003 | Ng et al. |
| 2003/0069510 A1 | 4/2003 | Semler |
| 2003/0191445 A1 | 10/2003 | Wallen et al. |
| 2003/0212319 A1 | 11/2003 | Magill |
| 2003/0212340 A1 | 11/2003 | Lussier et al. |
| 2003/0229809 A1 | 12/2003 | Wexler et al. |
| 2004/0015058 A1 | 1/2004 | Besson et al. |
| 2004/0030259 A1 | 2/2004 | Dae et al. |
| 2004/0062133 A1 | 4/2004 | Tsuji |
| 2004/0073132 A1 | 4/2004 | Maahs et al. |
| 2004/0116822 A1 | 6/2004 | Lindsey |
| 2004/0165646 A1 | 8/2004 | Shidemantle et al. |
| 2004/0215098 A1 | 10/2004 | Barton et al. |
| 2004/0220538 A1 | 11/2004 | Panopoulos |
| 2004/0236188 A1 | 11/2004 | Hutchinson et al. |
| 2005/0085706 A1 | 4/2005 | Perrault et al. |
| 2005/0101843 A1 | 5/2005 | Quinn et al. |
| 2005/0131288 A1 | 6/2005 | Turner et al. |
| 2005/0159653 A1 | 7/2005 | Iijima et al. |
| 2005/0195079 A1 | 9/2005 | Cohen |
| 2005/0228297 A1 | 10/2005 | Banet et al. |
| 2005/0228299 A1 | 10/2005 | Banet |
| 2005/0231350 A1 | 10/2005 | Littrell et al. |
| 2005/0245831 A1 | 11/2005 | Banet |
| 2005/0245839 A1 | 11/2005 | Stivoric et al. |
| 2005/0249263 A1 | 11/2005 | Yerlikaya et al. |
| 2005/0251128 A1 | 11/2005 | Amoah |
| 2005/0277841 A1 * | 12/2005 | Shennib ............... A61B 5/4362 600/511 |
| 2005/0280531 A1 | 12/2005 | Fadem et al. |
| 2006/0009697 A1 | 1/2006 | Banet et al. |
| 2006/0031102 A1 | 2/2006 | Teller |
| 2006/0045165 A1 | 3/2006 | Chan et al. |

(56) References Cited

U.S. PATENT DOCUMENTS

| | | |
|---|---|---|
| 2006/0047987 A1 | 3/2006 | Prabhakaran et al. |
| 2006/0094971 A1 | 5/2006 | Drew |
| 2006/0098576 A1 | 5/2006 | Brownrigg et al. |
| 2006/0155183 A1 | 7/2006 | Kroecker et al. |
| 2006/0202816 A1 | 9/2006 | Crump et al. |
| 2006/0224072 A1* | 10/2006 | Shennib ............... A61B 5/6833 600/509 |
| 2006/0224349 A1 | 10/2006 | Butterfield |
| 2006/0276714 A1 | 12/2006 | Holt et al. |
| 2007/0032706 A1 | 2/2007 | Kamath et al. |
| 2007/0041424 A1 | 2/2007 | Lev et al. |
| 2007/0099678 A1 | 5/2007 | Kim et al. |
| 2007/0116089 A1 | 5/2007 | Bisch et al. |
| 2007/0123756 A1 | 5/2007 | Kitajima et al. |
| 2007/0129622 A1 | 6/2007 | Bourget et al. |
| 2007/0135866 A1 | 6/2007 | Baker et al. |
| 2007/0142715 A1 | 6/2007 | Banet et al. |
| 2007/0185660 A1 | 8/2007 | Anderson |
| 2007/0191728 A1 | 8/2007 | Shennib |
| 2007/0208233 A1 | 9/2007 | Kovacs |
| 2007/0219434 A1 | 9/2007 | Abreu |
| 2007/0225614 A1 | 9/2007 | Naghavi et al. |
| 2007/0255184 A1* | 11/2007 | Shennib ............... A61B 5/6833 600/591 |
| 2007/0293781 A1 | 12/2007 | Sims et al. |
| 2008/0042866 A1 | 2/2008 | Morse et al. |
| 2008/0091090 A1* | 4/2008 | Guillory ............... A61B 5/6814 600/301 |
| 2008/0097178 A1 | 4/2008 | Banet et al. |
| 2008/0097422 A1 | 4/2008 | Edwards et al. |
| 2008/0114220 A1 | 5/2008 | Banet et al. |
| 2008/0119707 A1 | 5/2008 | Stafford |
| 2008/0143512 A1 | 6/2008 | Wakisaka et al. |
| 2008/0183054 A1 | 7/2008 | Kroeger et al. |
| 2008/0200770 A1 | 8/2008 | Hubinette |
| 2008/0200774 A1 | 8/2008 | Luo |
| 2008/0208026 A1 | 8/2008 | Noujaim et al. |
| 2008/0214949 A1 | 9/2008 | Stivoric et al. |
| 2008/0221399 A1 | 9/2008 | Zhou et al. |
| 2008/0234600 A1 | 9/2008 | Marsh |
| 2008/0275327 A1 | 11/2008 | Faarbaek et al. |
| 2008/0281180 A1* | 11/2008 | Choe ................... A61N 1/0408 600/391 |
| 2008/0294058 A1* | 11/2008 | Shklarski ........... A61B 5/02055 600/502 |
| 2008/0294065 A1 | 11/2008 | Waldhoff et al. |
| 2008/0305154 A1 | 12/2008 | Yanaki |
| 2009/0018409 A1 | 1/2009 | Banet et al. |
| 2009/0054737 A1 | 2/2009 | Magar et al. |
| 2009/0062670 A1* | 3/2009 | Sterling ............. A61B 5/04085 600/509 |
| 2009/0069642 A1 | 3/2009 | Gao et al. |
| 2009/0073991 A1* | 3/2009 | Landrum ............. A61B 5/0006 370/400 |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076345 A1 | 3/2009 | Manicka et al. |
| 2009/0076346 A1 | 3/2009 | James et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076405 A1 | 3/2009 | Amurthur et al. |
| 2009/0076559 A1 | 3/2009 | Libbus et al. |
| 2009/0105549 A1 | 4/2009 | Smith et al. |
| 2009/0105605 A1 | 4/2009 | Abreu |
| 2009/0131759 A1 | 5/2009 | Sims et al. |
| 2009/0131774 A1 | 5/2009 | Sweitzer et al. |
| 2009/0182204 A1 | 7/2009 | Semler et al. |
| 2009/0203974 A1 | 8/2009 | Hickle |
| 2009/0209896 A1 | 8/2009 | Selevan |
| 2009/0227877 A1 | 9/2009 | Tran |
| 2009/0259139 A1 | 10/2009 | Stepien et al. |
| 2009/0270744 A1 | 10/2009 | Prstojevich et al. |
| 2009/0271681 A1 | 10/2009 | Piret et al. |
| 2009/0306536 A1 | 12/2009 | Ranganathan et al. |
| 2010/0010319 A1 | 1/2010 | Tivig et al. |
| 2010/0036212 A1 | 2/2010 | Rieth |
| 2010/0056886 A1 | 3/2010 | Hurtubise et al. |
| 2010/0056945 A1 | 3/2010 | Holmes |
| 2010/0056946 A1 | 3/2010 | Holmes |
| 2010/0056947 A1 | 3/2010 | Holmes |
| 2010/0081949 A1 | 4/2010 | Derby, Jr. |
| 2010/0100004 A1 | 4/2010 | van Someren |
| 2010/0113894 A1 | 5/2010 | Padiy |
| 2010/0121217 A1 | 5/2010 | Padiy et al. |
| 2010/0160745 A1 | 6/2010 | Hills et al. |
| 2010/0198038 A1* | 8/2010 | Nagata ................. A61B 5/282 600/372 |
| 2010/0222688 A1 | 9/2010 | Fischell et al. |
| 2010/0234716 A1 | 9/2010 | Engel |
| 2010/0249541 A1 | 9/2010 | Geva et al. |
| 2010/0249625 A1 | 9/2010 | Lin |
| 2010/0286607 A1 | 11/2010 | Saltzstein |
| 2010/0292605 A1 | 11/2010 | Grassl et al. |
| 2010/0298656 A1 | 11/2010 | McCombie et al. |
| 2010/0298895 A1 | 11/2010 | Ghaffari et al. |
| 2010/0323634 A1 | 12/2010 | Kimura |
| 2010/0324548 A1 | 12/2010 | Godara et al. |
| 2011/0004076 A1 | 1/2011 | Janna et al. |
| 2011/0060252 A1 | 3/2011 | Simonsen et al. |
| 2011/0066062 A1 | 3/2011 | Banet et al. |
| 2011/0077497 A1 | 3/2011 | Oster et al. |
| 2011/0144470 A1 | 6/2011 | Mazar et al. |
| 2011/0160601 A1* | 6/2011 | Wang ................. A61B 5/04085 600/509 |
| 2011/0176465 A1 | 7/2011 | Panta et al. |
| 2011/0182213 A1 | 7/2011 | Forssell et al. |
| 2011/0224557 A1 | 9/2011 | Banet et al. |
| 2011/0237922 A1* | 9/2011 | Parker, III ........... A61B 5/0006 600/382 |
| 2012/0029300 A1 | 2/2012 | Paquet |
| 2012/0029306 A1 | 2/2012 | Paquet et al. |
| 2012/0029307 A1 | 2/2012 | Paquet et al. |
| 2012/0029308 A1 | 2/2012 | Paquet |
| 2012/0029309 A1 | 2/2012 | Paquet et al. |
| 2012/0029310 A1 | 2/2012 | Paquet et al. |
| 2012/0029311 A1 | 2/2012 | Raptis et al. |
| 2012/0029312 A1 | 2/2012 | Beaudry et al. |
| 2012/0029313 A1 | 2/2012 | Burdett et al. |
| 2012/0029314 A1 | 2/2012 | Paquet et al. |
| 2012/0029315 A1 | 2/2012 | Raptis et al. |
| 2012/0029316 A1 | 2/2012 | Raptis et al. |
| 2012/0030547 A1 | 2/2012 | Raptis et al. |
| 2012/0108920 A1 | 5/2012 | Bly et al. |
| 2012/0165621 A1 | 6/2012 | Grayzel et al. |
| 2012/0238901 A1 | 9/2012 | Augustine |
| 2012/0310070 A1 | 12/2012 | Kumar et al. |
| 2014/0350362 A1 | 11/2014 | Raptis et al. |
| 2015/0223706 A1 | 8/2015 | Raptis et al. |
| 2015/0272515 A1 | 10/2015 | Paquet et al. |

FOREIGN PATENT DOCUMENTS

| | | |
|---|---|---|
| JP | 2002507131 A | 3/2002 |
| JP | 2004503266 A | 2/2004 |
| JP | 2005521453 A | 7/2005 |
| JP | 2009544065 A | 12/2009 |
| KR | 20070097725 A | 10/2007 |
| KR | 100949150 B1 | 3/2010 |
| WO | WO-1990012606 A2 | 11/1990 |

OTHER PUBLICATIONS

Akyldiz, I.F. et al; "Wireless Multemedia Sensor Networks; a Survey". IEEE Wireless Communications. Dec. 2007, p. 32-39.

Arisha, K. et al. in "System-Level Power Optimization for wireless Multimedia Communicatioin". Editors: Ramesh, K and Goodman, D.; Springer US; 2002, p. 21-40.

(56) References Cited

OTHER PUBLICATIONS

Brown, B.H. et al., "Bipolar and Tetrapolar transfer impedence measurements from volume conductor," Electronics Letters, Wol. 35, No. 25, 2000, pp. 2060-2062.
Cardei, M. et al; "Improving Wireless Sensor Network Lifteim through Power Aware Ogranization"; Wireless Networks 11, 333-340, 2005.
Cooley, W.L. et al. "A new design for an impedance pneumograph," Journal of Applied Physiology, vol. 25, No. 4, 1968, pp. 429-432.
Davidson, K.G. et al., "Measurement of tidal volume by using transthoracic impedance variations in rats," J. Appl. Physiol. 86: 759-766, 1999.
Ernst, J.M. et al, "Impedence Penumography; noise as signal in impednace cardiography," Psychophysiology, 36 (1999) 333-338.
Freundlich J.J. et al., Electrical Impedence Pneumography for Simple Nonrestritive Continuous Monitoring of Respiratory Rate, Rhythm and Tidal Volume for Surgical Patients, Chest, 65, p. 181-184, 1974.
Grenvik, A. et al., "Impedence Pneumography," Chest , vol. 62, No. 4, Oct. 1972, pp. 439-443.
Herman, T. et al.; "A Distributed TDMA Slot Assignment Algorithm for Wireless Sensor Networks"; S. Nikoletseas and J. Rolim (Eds.): Algosensors 2004, LNCS 3121, pp. 45-58, 2004, Springer-Verlag Berlin Heidelberg 2004.
Hohlt, B. et al. "Flexible Power Scheduling for Sensor Networks", IPSN'04, Apr. 26-27, 2004, Berkeley, California, USA. p. 1-10.
Holt, T. et al., "Monitoring and recording of physiological data of the manned space flight program," Supplement to IEEE Transactions on Aerospace, Jun. 1965, p. 341-344.
International Preliminary Report on Patentability in International Application No. PCT/US2011/030088, dated Oct. 27, 2012, 13 pages.
International Preliminary Report on Patentability in International Application No. PCT/US2011/045240, dated Jan. 29, 2013, 6 pages.
International Preliminary Report on Patentability in International Application No. PCT/US2011/045245, dated Jan. 29, 2013, 5 pages.
International Preliminary Report on Patentability in International Application No. PCT/US2011/045249, dated Jan. 29, 2013, 4 pages.
International Preliminary Report on Patentability in International Application No. PCT/US2011/045256, dated Jan. 29, 2013, 4 pages.
International Preliminary Report on Patentability in International Application No. PCT/US2011/045258, dated Jan. 29, 2013, 5 pages.
International Preliminary Report on Patentability in International Application No. PCT/US2011/045337, dated Jan. 9, 2013, 4 pages.
International Preliminary Report on Patentability in International Application No. PCT/US2011/045361, dated Jan. 29, 2013, 6 pages.
International Preliminary Report on Patentability in International Application No. PCT/US2011/045408, dated Jan. 29, 2013, 4 pages.
International Preliminary Report on Patentability in International Application No. PCT/US2011/045414, dated Jan. 29, 2013, 6 pages.
International Preliminary Report on Patentability in International Application No. PCT/US2011/045415, dated Jan. 29, 2013, 4 pages.
International Preliminary Report on Patentability in International Application No. PCT/US2011/045419, dated Jan. 29, 2013, 5 pages.
International Preliminary Report on Patentability in International Application No. PCT/US2011/045425, dated Jan. 29, 2013, 5 pages.
international Search Report and Written Opinion for International Application No. PCT/US2011/045408, dated Feb. 24, 2012, 6 pages.
International Search Report and Written Opinion in International Application No. PCT/US2011/045361, dated Apr. 6, 2012, 8 pages.
International Search Report and Written Opinion in International Application No. PCT/US2011/030088, dated Oct. 31, 2011, 7 pages.
International Search Report and Written Opinion in International Application No. PCT/US2011/045240, dated Mar. 15, 2012, 8 pages.
International Search Report and Written Opinion in International Application No. PCT/US2011/045245, dated Mar. 28, 2012, 7 pages.
International Search Report and Written Opinion in International Application No. PCT/US2011/045249, dated Mar. 12, 2012, 6 pages.
International Search Report and Written Opinion in International Application No. PCT/US2011/045256, dated Feb. 9, 2012, 12 pages.
International Search Report and Written Opinion in International Application No. PCT/US2011/045258, dated Apr. 6, 2012, 12 pages.
International Search Report and Written Opinion in International Application No. PCT/US2011/045337, dated Feb. 9, 2012, 7 pages.
International Search Report and Written Opinion in International Application No. PCT/US2011/045414, dated Feb. 24, 2012, 9 pages.
International Search Report and Written Opinion in International Application No. PCT/US2011/045415, dated Feb. 24, 2012, 7 pages.
International Search Report and Written Opinion in International Application No. PCT/US2011/045419, dated Apr. 6, 2012, 7 pages.
International Search Report and Written Opinion in International Application No. PCT/US2011/045425, dated Apr. 6, 2012, 7 pages.
Kelkar, S.P. et al., "Development of Movement artifact free breathing monitor," J. Instrum. Soc. India 38(1) 34-43, 2008.
Kessler, "TCP/IP and tcpdump Pocket reference Guide", Champlain College, 2006.
Lee, W. L. et al; "FlexiTP: A Flexible-Schedule-Based TDMA Protocol for Fault-Tolerant and energy-Efficient Wireless Sensor Networks", IEEE transactions on Parallel and Distributed Systems, vol. 19, No. 6, Jun. 2008; p. 851-864.
Lee, W.L.; "Flexible-Schedule-Based TDMA Protocols for Supporting Fault-Tolerance, On-Demand TDMA Slot Transfer, and Peer-to-Peer Communication in Wireless Sensor Networks"; Thesis for the degree of Doctor in Philosophy, University of Western Australia, 2007, p. 1-213.
Loriga, G., et al., "Textile sensing interfaces for cardiopulmonary signs monitoring," Proceedings of the 2005 IEEE Engineering in Medicine and Biology 27th Annual Conference Shanghai, China, Sep. 1-4, 2005, p. 7349-7352.
Luo, S. et al "The electrode system in Impedance-Based Ventilation Measurement", IEEE Transactions of Biomedical Engineering, vol. 39, No. 11, Nov. 1992, p. 1130-1140.
Matthews, R., et al., "A Wearable Physiological Sensor Suite for Unobstrusive Monitoring of Physiological and Cognitive State," Proceedings of the 29th annual International Conference of the IEEE EMBS Cite Internationale, Lyon, France, Aug. 23-26, 2007.
Miller, Matthew J., et al., "On-Demand Tdma Scheduling for energy Conservation in Sensor Networks," Technical Report, Jun. 2004.
Murat, B., "Electrical Impedance Plethysmography," Wiley Encyclopedia of Biomedical Engineering , 2006, p. 1-10.
NPL_VitalSense_2006, p. 1-2.
Pacela, A. "Impedance Pneumogrpahy—a survey of Instrumentation Techniques" Med. & Biol. Engng. vol. 4, pp. 1-15, 1996.
Pantazis, N. A. et al; "Energy efficiency in wireless sensor networks using sleep mode TDMA scheduling", Ad Hoc Networks 7 (2009) 322-343.
Paradiso, R. et al "A wearalbe health care system based on knitted integrated sensors", IEEE transactions on Information Technology in Biomedicine, vol. 9, No. 3, Sep. 2005, p. 337-344.
Park, et al., "Development of Flexible Self Adhesive Patch for Professional Heat Stress Monitoring Service," Proceedings of the 2005 IEEE Engineering in Medicine and Biology 27th Annual Conference Shanghai, China, Sep. 1-4, 2005, pp. 3789-3792.
Poon, C.S. et al., "Evaluation of two noninvasive techniques for exercise ventilatory measurements," IEEE Engineering in Medicine and Biology Conference, 1988, pp. 0823-0824.
Rashid, R. A. et al; "Development of Energy Aware TDMA-Based MAC Protocol for Wireless Sensor Network System", European Journal of Scientific Research, vol. 30 No. 4 (2009), pp. 571-578.
Shakian, A.V. et al., "electrode Motion Artifacts in electrical Impedence Pneumography," IEEE Transactions in Biomedical Engineering, vol. BME-32, No. 6, Jun. 1985, pp. 448-451.
Shaw, G.A. et al., "Warfighter Physiological and Environmental Monitoring: A Study for the U.S. Army Research Institute in

(56) References Cited

OTHER PUBLICATIONS

Environmental Medicine and the Soldier Systems Center," 2004, Lincoln Laboratory, MIT, pp. 1-141.
Zheng, W.W. et al; "Adaptive-frame based Dynamic Slot Assignment Protocol for Tactical Data Link Systems", 2009 International Conference on Networks Security, Wireless Communications and Trusted Computing, IEEE, p. 709-714.
Zhihui Chen; Kohkhar, A. "Self organization and energy efficient TDMA MAC protocol by wake up for wireless sensor networks," Sensor and Ad Hoc Communications and Networks, 2004. IEEE SECON 2004. 2004 First Annual IEEE Communications Society Conference on, pp. 335-341. Oct. 2004.

* cited by examiner

VITAL-SIGNS PATCH HAVING A STRAIN RELIEF

CROSS-REFERENCES TO RELATED APPLICATIONS

The present application claims the benefit of priority under 35 U.S.C. § 120 as a divisional of U.S. patent application Ser. No. 12/844,774 entitled "Vital-Signs Patch Having a Strain Relief," and filed on Jul. 27, 2010, issued as U.S. Pat. No. 9,585,620, on Mar. 7, 2017, the disclosure of which is hereby incorporated by reference in its entirety for all purposes. The following applications disclose certain common subject matter with the present application: "A Vital-Signs Monitor with Encapsulation Arrangement," Ser. No. 12/844,766; "A Vital-Signs Monitor with Spaced Electrodes," Ser. No. 12/844,769; "A Vital-Signs Patch Having a Strain Relief," Ser. No. 12/844,774; "A Temperature Probe Suitable for Axillary Reading," Ser. No. 12/844,775; "System and Method for Monitoring Body Temperature of a Person," Ser. No. 12/844,771; "System and Method for Saving Battery Power in a Vital Signs Monitor," Ser. No. 12/844,789; "A System and Method for Conserving Battery Power in a Patient Monitoring System," Ser. No. 12/844,796; "A System and Method for Saving Battery Power in a Patient Monitoring System," Ser. No. 12/844,801; "A System And Method for Tracking Vital-Signs Monitor Patches," Ser. No. 12/844,788; "A System And Method for Reducing False Alarms Associated with Vital-Signs Monitoring," Ser. No. 12/844,794; "A System And Method for Location Tracking of Patients in a Vital-Signs Monitoring System," Ser. No. 12/844,781; "A System And Method for Reducing False Alarms Based on Motion and Location Sensing," Ser. No. 12/844,765; all of the listed applications filed on Jul. 27, 2010.

BACKGROUND

Field

The present disclosure generally relates to systems and methods of physiological monitoring, and, in particular, relates to monitoring of vital signs of patients.

Description of the Related Art

Some of the most basic indicators of a person's health are those physiological measurements that reflect basic body functions and are commonly referred to as a person's "vital signs." The four measurements commonly considered to be vital signs are body temperature, pulse rate, blood pressure, and respiratory rate. Some clinicians consider oxygen saturation ($S_{O2}$) to be a "fifth vital sign" particularly for pediatric or geriatric cases. Some or all of these measurements may be performed routinely upon a patient when they arrive at a healthcare facility, whether it is a routine visit to their doctor or arrival at an Emergency Room (ER).

Vital signs are frequently taken by a nurse using basic tools including a thermometer to measure body temperature, a sphygmomanometer to measure blood pressure, and a watch to count the number of breaths or the number of heart beats in a defined period of time which is then converted to a "per minute" rate. If a patient's pulse is weak, it may not be possible to detect a pulse by hand and the nurse may use a stethoscope to amplify the sound of the patient's heart beat so that she can count the beats. Oxygen saturation of the blood is most easily measured with a pulse oximeter.

When a patient is admitted to a hospital, it is common for vital signs to be measured and recorded at regular intervals during the patient's stay to monitor their condition. A typical interval is 4 hours, which leads to the undesirable requirement for a nurse to awaken a patient in the middle of the night to take vital sign measurements.

When a patient is admitted to an ER, it is common for a nurse to do a "triage" assessment of the patient's condition that will determine how quickly the patient receives treatment. During busy times in an ER, a patient who does not appear to have a life-threatening injury may wait for hours until more-serious cases have been treated. While the patient may be reassessed at intervals while awaiting treatment, the patient may not be under observation between these reassessments.

Measuring certain vital signs is normally intrusive at best and difficult to do on a continuous basis. Measurement of body temperature, for example, is commonly done by placing an oral thermometer under the tongue or placing an infrared thermometer in the ear canal such that the tympanic membrane, which shared blood circulation with the brain, is in the sensor's field of view. Another method of taking a body temperature is by placing a thermometer under the arm, referred to as an "axillary" measurement as axilla is the Latin word for armpit. Skin temperature can be measured using a stick-on strip that may contain panels that change color to indicate the temperature of the skin below the strip.

Measurement of respiration is easy for a nurse to do, but relatively complicated for equipment to achieve. A method of automatically measuring respiration is to encircle the upper torso with a flexible band that can detect the physical expansion of the rib cage when a patient inhales. An alternate technique is to measure a high-frequency electrical impedance between two electrodes placed on the torso and detect the change in impedance created when the lungs fill with air. The electrodes are typically placed on opposite sides of one or both lungs, resulting in placement on the front and back or on the left and right sides of the torso, commonly done with adhesive electrodes connected by wires or by using a torso band with multiple electrodes in the strap.

Measurement of pulse is also relatively easy for a nurse to do and intrusive for equipment to achieve. A common automatic method of measuring a pulse is to use an electrocardiograph (ECG or EKG) to detect the electrical activity of the heart. An EKG machine may use 12 electrodes placed at defined points on the body to detect various signals associated with the heart function. Another common piece of equipment is simply called a "heart rate monitor." Widely sold for use in exercise and training, heart rate monitors commonly consist of a torso band, in which are embedded two electrodes held against the skin and a small electronics package. Such heart rate monitors can communicate wirelessly to other equipment such as a small device that is worn like a wristwatch and that can transfer data wirelessly to a PC.

Nurses are expected to provide complete care to an assigned number of patients. The workload of a typical nurse is increasing, driven by a combination of a continuing shortage of nurses, an increase in the number of formal procedures that must be followed, and an expectation of increased documentation. Replacing the manual measurement and logging of vital signs with a system that measures and records vital signs would enable a nurse to spend more time on other activities and avoid the potential for error that is inherent in any manual procedure.

SUMMARY

For some or all of the reasons listed above, there is a need to be able to continuously monitor patients in different settings. In addition, it is desirable for this monitoring to be done with limited interference with a patient's mobility or interfering with their other activities.

Embodiments of the patient monitoring system disclosed herein measure certain vital signs of a patient, which include respiratory rate, pulse rate, blood pressure, body temperature, and, in some cases, oxygen saturation ($S_{O2}$), on a regular basis and compare these measurements to defined limits.

In certain aspects of the present disclosure, a vital-signs patch is provided that includes at least two electrodes and a circuit assembly that periodically take at least one measurement from the electrodes. The patch is a unitized device that contains the circuit assembly with the electrodes on the underside of the patch. The patch can be attached to a patient with the electrodes in electrical contact with the patient's skin. The segments of the patch that connect the electrodes to the circuit assembly are flexible, which reduces the noise induced in the measurement by stress on the contact between the electrodes and the patient.

In certain aspects of the present disclosure, a vital-signs patch is provided that includes a patch housing having a circuit housing portion and at least one flexible electrode portion, a circuit assembly, and at least one electrode. The electrode is attached to the electrode portion of the patch housing and configured for attaching the patch housing to the skin of the patient.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
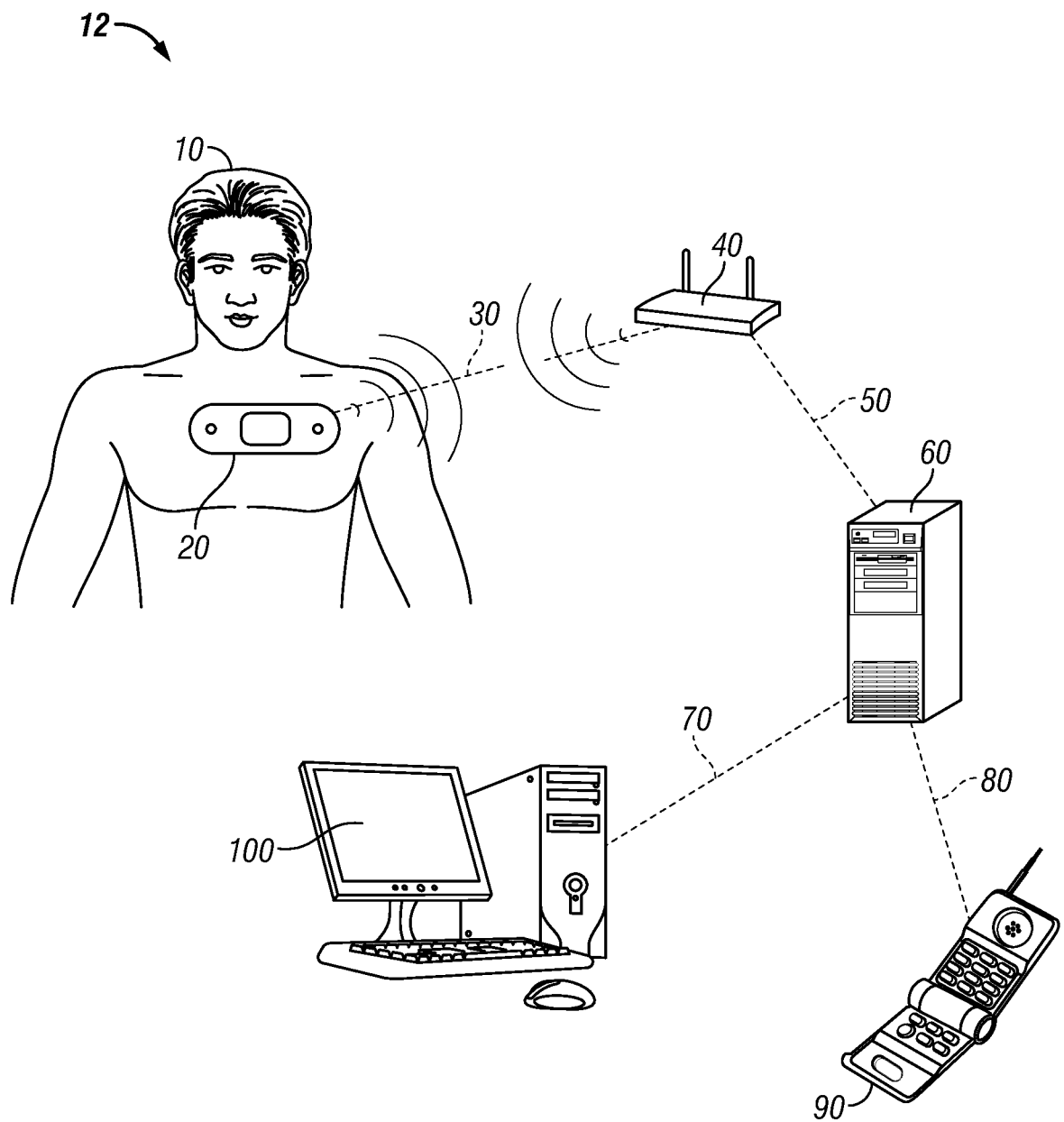
FIG. 1 is a diagram illustrating an exemplary embodiment of a patient monitoring system according to certain aspects of the present disclosure.

Periodic monitoring of patients in a hospital is desirable at least to ensure that patients do not suffer an un-noticed sudden deterioration in their condition or a secondary injury during their stay in the hospital. It is impractical to provide continuous monitoring by a clinician and cumbersome to connect sensors to a patient, which are then connected to a fixed monitoring instrument by wires. Furthermore, systems that sound an alarm when the measured value exceeds a threshold value may sound alarms so often and in situations that are not truly serious that such alarms are ignored by clinicians.

Measuring vital signs is difficult to do on a continuous basis. Accurate measurement of cardiac pulse, for example, can be done using an electrocardiograph (ECG or EKG) to detect the electrical activity of the heart. An EKG machine may use up to 12 electrodes placed at various points on the body to detect various signals associated with the cardiac function. Another common piece of equipment is termed a "heart rate monitor." Widely sold for use in exercise and physical training, heart rate monitors may comprise a torso band in which are embedded two electrodes held against the skin and a small electronics package. Such heart rate monitors can communicate wirelessly to other equipment such as a small device that is worn like a wristwatch and that can transfer data wirelessly to a personal computer (PC).

Monitoring of patients that is referred to as "continuous" is frequently periodic, in that measurements are taken at intervals. In many cases, the process to make a single measurement takes a certain amount of time, such that even back-to-back measurements produce values at an interval equal to the time that it takes to make the measurement. For the purpose of vital sign measurement, a sequence of repeated measurements can be considered to be "continuous" when the vital sign is not likely to change an amount that is of clinical significance within the interval between measurements. For example, a measurement of blood pressure every 10 minutes may be considered "continuous" if it is considered unlikely that a patient's blood pressure can change by a clinically significant amount within 10 minutes. The interval appropriate for measurements to be considered continuous may depend on a variety of factors including the type of injury or treatment and the patient's medical history. Compared to intervals of 4-8 hours for manual vital sign measurement in a hospital, measurement intervals of 30 minutes to several hours may still be considered "continuous."

Certain exemplary embodiments of the present disclosure include a system that comprises a vital-signs monitor patch that is attached to the patient, and a bridge that communicates with monitor patches and links them to a central server that processes the data, where the server can send data and alarms to a hospital system according to algorithms and protocols defined by the hospital.

The construction of the vital-signs monitor patch is described according to certain aspects of the present disclosure. As the patch may be worn continuously for a period of time that may be several days, as is described in the following disclosure, it is desirable to encapsulate the components of the patch such that the patient can bathe or shower and engage in their normal activities without degradation of the patch function. An exemplary configuration of the construction of the patch to provide a hermetically sealed enclosure about the electronics is disclosed.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

FIG. 1 discloses a vital sign monitoring system according to certain embodiments of the present disclosure. The vital sign monitoring system 12 includes vital-signs monitor patch 20, bridge 40, and surveillance server 60 that can send messages or interact with peripheral devices exemplified by mobile device 90 and workstation 100.

Monitor patch 20 resembles a large adhesive bandage and is applied to a patient 10 when in use. It is preferable to apply the monitor patch 20 to the upper chest of the patient 10 although other locations may be appropriate in some circumstances. Monitor patch 20 incorporates one or more electrodes (not shown) that are in contact with the skin of patient 10 to measure vital signs such as cardiac pulse rate and respiration rate. Monitor patch 20 also may include other sensors such as an accelerometer, temperature sensor, or oxygen saturation sensor to measure other characteristics associated with the patient. These other sensors may be internal to the monitor patch 20 or external sensors that are operably connected to the monitor patch 20 via a cable or wireless connection. Monitor patch 20 also includes a wireless transmitter that can both transmit and receive signals. This transmitter is preferably a short-range, low-power radio frequency (RF) device operating in one of the unlicensed radio bands. One band in the United States (US) is, for example, centered at 915 MHz and designated for industrial, scientific and medical (ISM) purposes. An example of an equivalent band in the European Union (EU) is centered at 868 MHz. Other frequencies of operation may be possible dependent upon the International Telecommunication Union (ITU), local regulations and interference from other wireless devices.

Surveillance server 60 may be a standard computer server connected to the hospital communication network and preferably located in the hospital data center or computer room, although other locations may be employed. The server 60 stores and processes signals related to the operation of the patient monitoring system 12 disclosed herein including the association of individual monitor patches 20 with patients 10 and measurement signals received from multiple monitor patches 20. Hence, although only a single patient 10 and monitor patch 20 are depicted in FIG. 1, the server 60 is able to monitor the monitor patches 20 for multiple patients 10.

Bridge 40 is a device that connects, or "bridges", between monitor patch 20 and server 60. Bridge 40 communicates with monitor patch 20 over communication link 30 operating, in these exemplary embodiments, at approximately 915 MHz and at a power level that enables communication link 30 to function up to a distance of approximately 10 meters. It is preferable to place a bridge 40 in each room and at regular intervals along hallways of the healthcare facility where it is desired to provide the ability to communicate with monitor patches 20. Bridge 40 also is able to communicate with server 60 over network link 50 using any of a variety of computer communication systems including hardwired and wireless Ethernet using protocols such as 802.11a/b/g or 802.3af. As the communication protocols of communication link 30 and network link 50 may be very different, bridge 40 provides data buffering and protocol conversion to enable bidirectional signal transmission between monitor patch 20 and server 60.

While the embodiments illustrated by FIG. 1 employ a bridge 20 to provide communication link between the monitor patch 20 and the server 60, in certain alternative embodiments, the monitor patch 20 may engage in direct wireless communication with the server 60. In such alternative embodiments, the server 60 itself or a wireless modem connected to the server 60 may include a wireless communication system to receive data from the monitor patch 20.

In use, a monitor patch 20 is applied to a patient 10 by a clinician when it is desirable to continuously monitor basic vital signs of patient 10 while patient 10 is, in this embodiment, in a hospital. Monitor patch 20 is intended to remain attached to patient 10 for an extended period of time, for example, up to 5 days in certain embodiments, limited by the battery life of monitor patch 20. In some embodiments, monitor patch 20 is disposable when removed from patient 10.

Server 60 executes analytical protocols on the measurement data that it receives from monitor patch 20 and provides this information to clinicians through external workstations 100, preferably personal computers (PCs), laptops, or smart phones, over the hospital network 70. Server 60 may also send messages to mobile devices 90, such as cell phones or pagers, over a mobile device link 80 if a measurement signal exceeds specified parameters. Mobile device link 80 may include the hospital network 70 and internal or external wireless communication systems that are capable of sending messages that can be received by mobile devices 90.

Figure 2A:
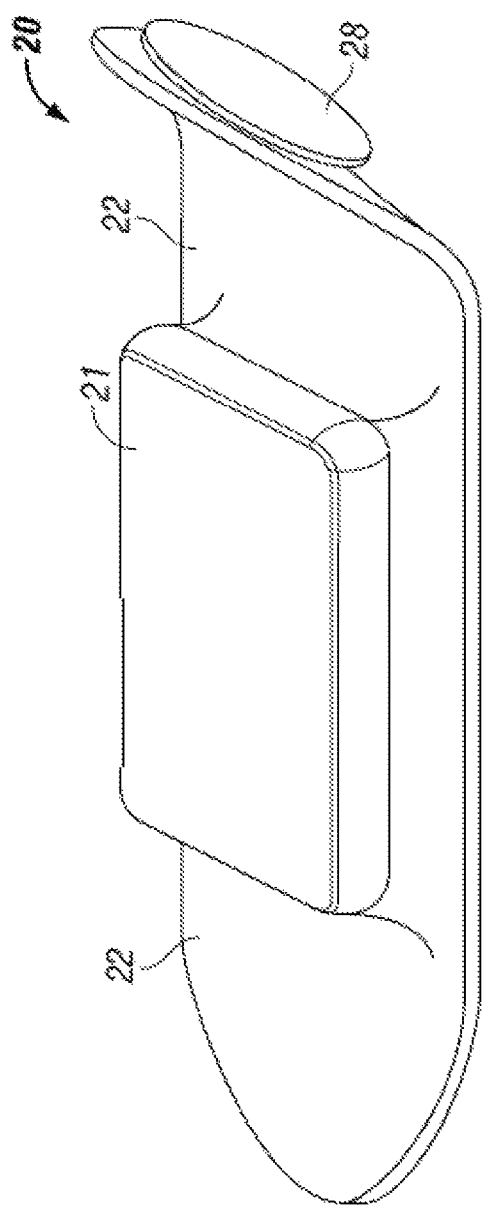
FIG. 2A is a perspective view of the vital-signs monitor patch of FIG. 1 according to certain aspects of the present disclosure.

FIG. 2A is a perspective view of the vital-signs monitor patch 20 shown in FIG. 1 according to certain aspects of the present disclosure. In the illustrated embodiment, the monitor patch 20 includes component carrier 23 comprising a central segment 21 and side segments 22 on opposing sides of the central segment 21. In certain embodiments, the central segment 21 is substantially rigid and includes a circuit assembly (24, FIG. 2B) having electronic components and battery mounted to a rigid printed circuit board (PCB). The side segments 22 are flexible and include a flexible conductive circuit (26, FIG. 2B) that connect the circuit assembly 24 to electrodes 28 disposed at each end of the monitor patch 20, with side segment 22 on the right shown as being bent upwards for purposes of illustration to make one of the electrodes 28 visible in this view.

Figure 2B:
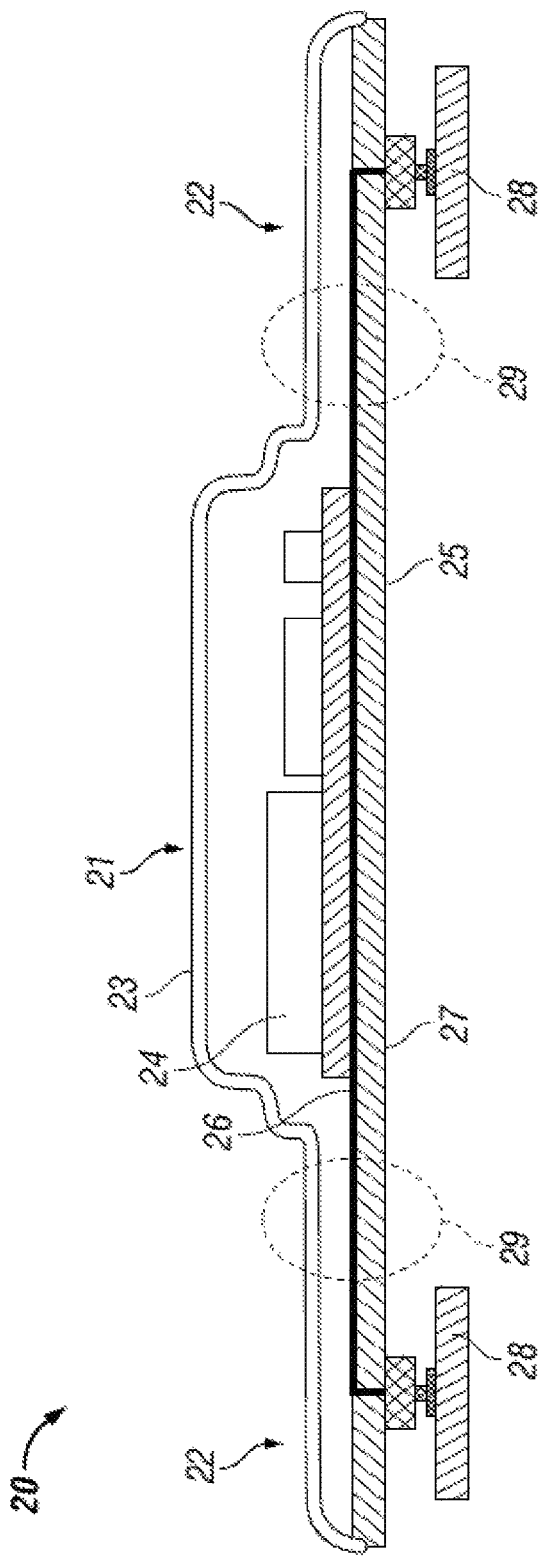
FIG. 2B is a cross-section of the vital-signs monitor patch of FIG. 1 according to certain aspects of the present disclosure.

FIG. 2B is a cross-sectional view of the vital-signs patch 20 shown in FIGS. 1 and 2A according to certain aspects of the present disclosure. The circuit assembly 24 and flexible conductive circuit 26 described above can be seen herein. The flexible conductive circuit 26 operably connects the circuit assembly 24 to the electrodes 28. Top and bottom layers 23 and 27 form a housing 25 that encapsulate circuit assembly 28 to provide a water and particulate barrier as well as mechanical protection. There are sealing areas on layers 23 and 27 that encircles circuit assembly 28 and is visible in the cross-section view of FIG. 2B as areas 29. Layers 23 and 27 are sealed to each other in this area to form a substantially hermetic seal. Within the context of certain aspects of the present disclosure, the term 'hermetic' implies that the rate of transmission of moisture through the seal is substantially the same as through the material of the layers that are sealed to each other, and further implies that the size of particulates that can pass through the seal are below the size that can have a significant effect on circuit assembly 24. Flexible conductive circuit 26 passes through portions of sealing areas 29 and the seal between layers 23 and 27 is maintained by sealing of layers 23 and 27 to flexible circuit assembly 28. The layers 23 and 27 are thin and flexible, as is the flexible conductive circuit 26, allowing the side segment 22 of the monitor patch 20 between the electrodes 28 and the circuit assembly 24 to bend as shown in FIG. 2A.

Figure 2C:
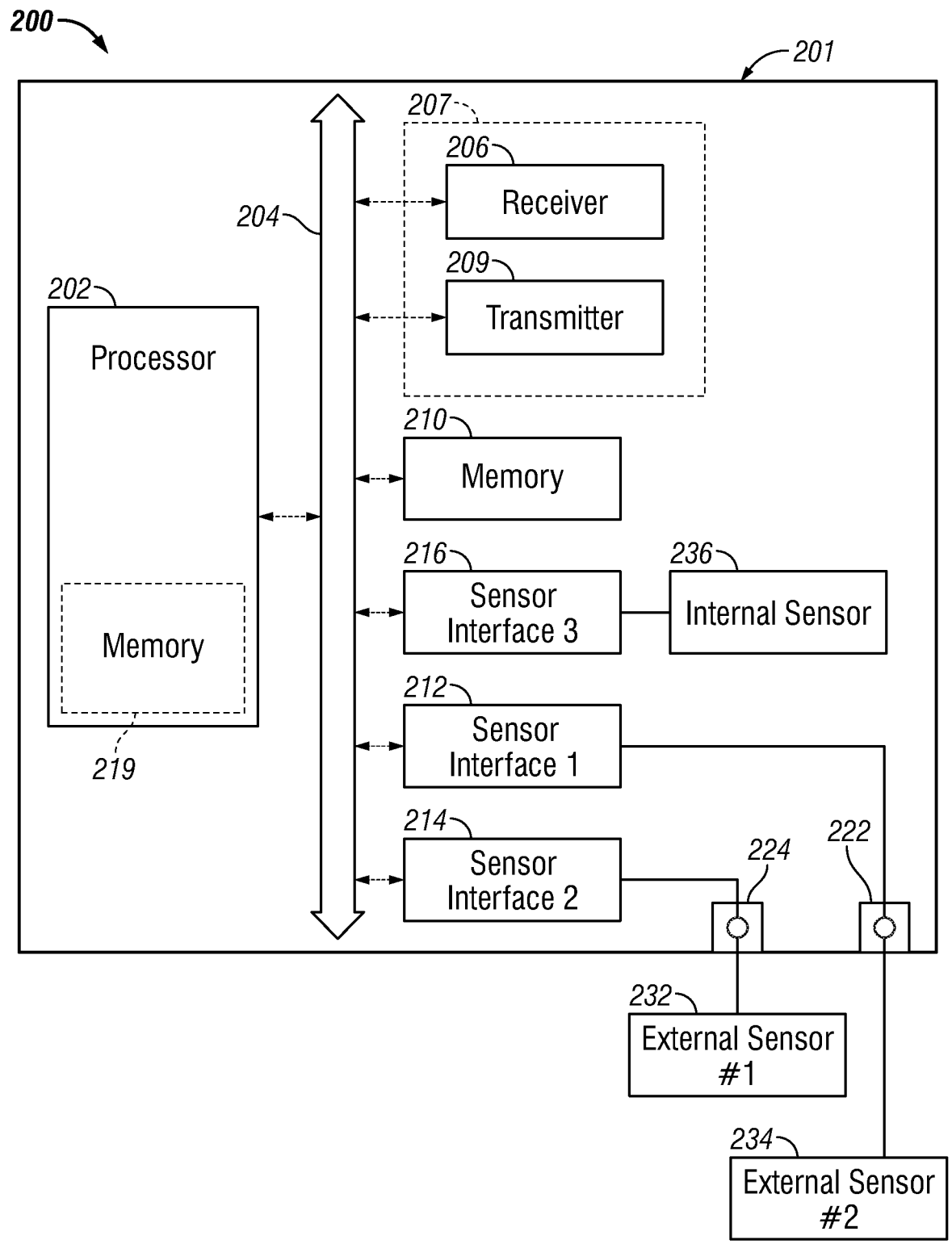
FIG. 2C is a functional block diagram illustrating exemplary electronic and sensor components of the vital-signs monitor patch of FIG. 1 according to certain aspects of the present disclosure.

FIG. 2C is a functional block diagram 200 illustrating exemplary electronic and sensor components of the monitor patch 20 of FIG. 1 according to certain aspects of the present disclosure. The block diagram 200 shows a processing and sensor interface module 201 and external sensors 232, 234 connected to the module 201. In the illustrated example, the module 201 includes a processor 202, a wireless transceiver 207 having a receiver 206 and a transmitter 209, a memory 210, a first sensor interface 212, a second sensor interface 214, a third sensor interface 216, and an internal sensor 236 connected to the third sensor interface 216. The first and second sensor interfaces 212 and 214 are connected to the first and second external sensors 232, 234 via first and second connection ports 222, 224, respectively. In certain embodiments, some or all of the aforementioned components of the module 201 and other components are mounted on a PCB.

Each of the sensor interfaces 212, 214, 216 can include one or more electronic components that are configured to generate an excitation signal or provide DC power for the sensor that the interface is connected to and/or to condition and digitize a sensor signal from the sensor. For example, the sensor interface can include a signal generator for generating an excitation signal or a voltage regulator for providing power to the sensor. The sensor interface can further include an amplifier for amplifying a sensor signal from the sensor and an analog-to-digital converter for digitizing the amplified sensor signal. The sensor interface can further include a filter (e.g., a low-pass or bandpass filter) for filtering out spurious noises (e.g., a 60 Hz noise pickup).

The processor 202 is configured to send and receive data (e.g., digitized signal or control data) to and from the sensor interfaces 212, 214, 216 via a bus 204, which can be one or more wire traces on the PCB. Although a bus communication topology is used in this embodiment, some or all communication between discrete components can also be implemented as direct links without departing from the scope of the present disclosure. For example, the processor 202 may send data representative of an excitation signal to the sensor excitation signal generator inside the sensor interface and receive data representative of the sensor signal from the sensor interface, over either a bus or direct data links between processor 202 and each of sensor interface 212, 214, and 216.

The processor 202 is also capable of communication with the receiver 206 and the transmitter 209 of the wireless transceiver 207 via the bus 204. For example, the processor 202 using the transmitter and receiver 209, 206 can transmit and receive data to and from the bridge 40. In certain embodiments, the transmitter 209 includes one or more of a RF signal generator (e.g., an oscillator), a modulator (a mixer), and a transmitting antenna; and the receiver 206 includes a demodulator (a mixer) and a receiving antenna which may or may not be the same as the transmitting antenna. In some embodiments, the transmitter 209 may include a digital-to-analog converter configured to receive data from the processor 202 and to generate a base signal; and/or the receiver 206 may include an analog-to-digital converter configured to digitize a demodulated base signal and output a stream of digitized data to the processor 202. In other embodiments, the radio may comprise a direct sequence radio, a software-defined radio, or an impulse spread spectrum radio.

The processor 202 may include a general-purpose processor or a specific-purpose processor for executing instructions and may further include a memory 219, such as a volatile or non-volatile memory, for storing data and/or instructions for software programs. The instructions, which may be stored in a memory 219 and/or 210, may be executed by the processor 202 to control and manage the wireless transceiver 207, the sensor interfaces 212, 214, 216, as well as provide other communication and processing functions.

The processor 202 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information, such as program instructions, data representative of sensor readings, preset alarm conditions, threshold limits, may be stored in a computer or processor readable medium such as a memory internal to the processor 202 (e.g., the memory 219) or a memory external to the processor 202 (e.g., the memory 210), such as a Random Access Memory (RAM), a flash memory, a Read Only Memory (ROM), a Programmable Read-Only Memory (PROM), an Erasable PROM (EPROM), registers, a hard disk, a removable disk, or any other suitable storage device.

In certain embodiments, the internal sensor 236 can be one or more sensors configured to measure certain properties of the processing and sensor interface module 201, such as a board temperature sensor thermally coupled to a PCB. In other embodiments, the internal sensor 236 can be one or more sensors configured to measure certain properties of the patient 10, such as a motion sensor (e.g., an accelerometer) for measuring the patient's motion or position with respect to gravity.

The external sensors 232, 234 can include sensors and sensing arrangements that are configured to produce a signal representative of one or more vital signs of the patient to which the monitor patch 20 is attached. For example, the first external sensor 232 can be a set of sensing electrodes that are affixed to an exterior surface of the monitor patch 20 and configured to be in contact with the patient for measuring the patient's respiratory rate, and the second external sensor 234 can include a temperature sensing element (e.g., a thermocouple or a thermistor or resistive thermal device (RTD)) affixed, either directly or via an interposing layer, to skin of the patient 10 for measuring the patient's body temperature. In other embodiments, one or more of the external sensors 232, 234 or one or more additional external sensors can measure other vital signs of the patient, such as blood pressure, pulse rate, or oxygen saturation.

Figure 3A:
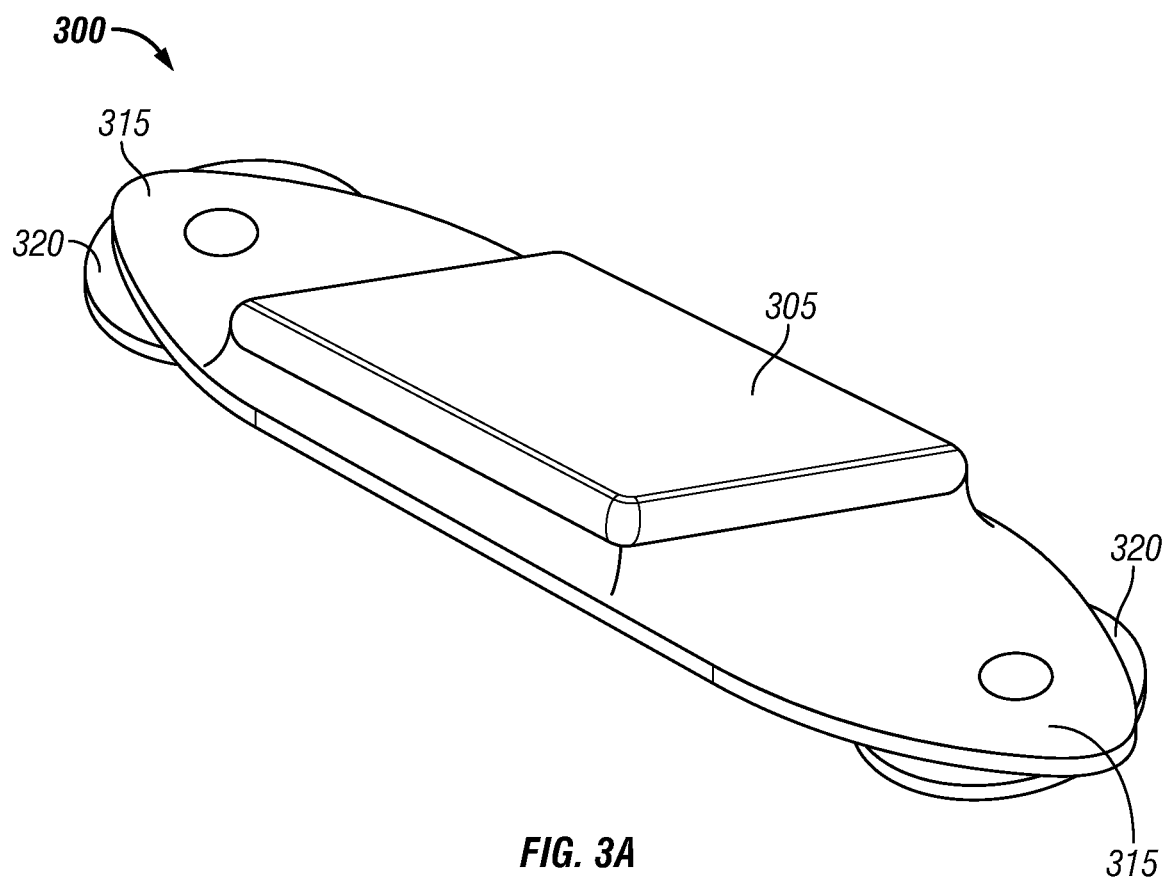
FIG. 3A is a perspective view of an exemplary embodiment of a patient monitoring system according to certain aspects of the present disclosure.

FIG. 3A is a perspective view of an exemplary embodiment of a patient monitoring system according to certain aspects of the subject disclosure. The unitized patch 300 has a central section 305 that contains the electronics of the patch. Electrodes 320 are shown attached to flaps 315 on opposite sides of section 305.

Figure 3B:
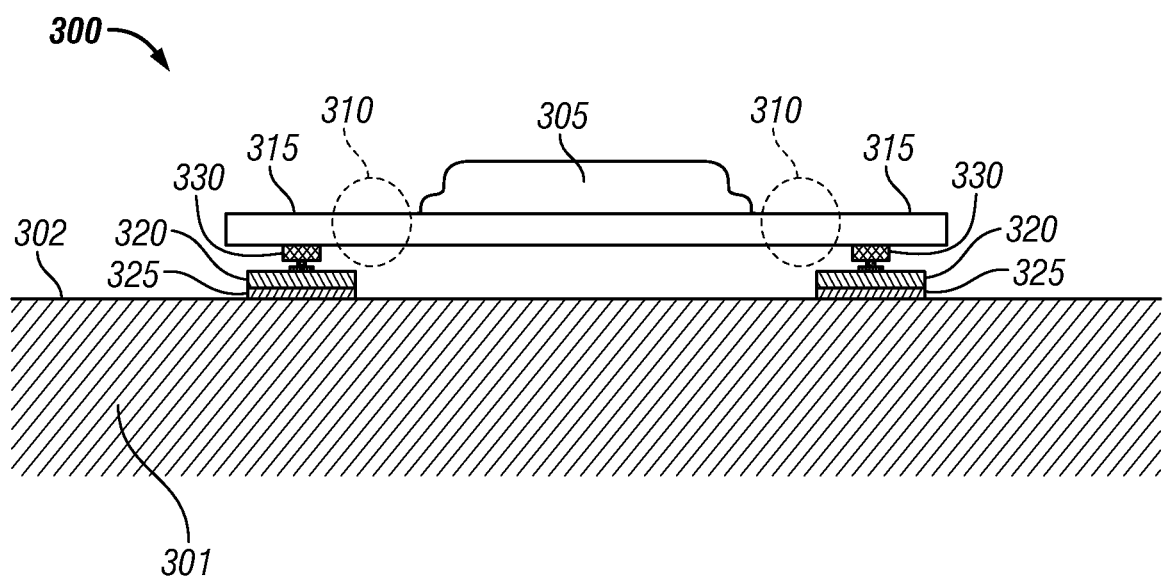
FIGS. 3B, 3C, and 3D are side views of the embodiment of FIG. 3A in various displaced configurations.

FIG. 3B is a side view of patch 300 of FIG. 3A in a configuration in which it is attached to a patient's body 301.

Electrodes 320 are adhered to the patient's skin 302 and are coupled to flaps 315 of patch 300 by a snap fitting 330 that is electrically conductive and disconnectable. The central section 305 is rigid, in these embodiments, as the circuit assembly incorporates a rigid printed circuit board (PCB). Flaps 315 have segments 310 that are flexible between the snap fitting 330 and the central section 305. Each electrode 330 comprises a layer of adhesive 325 on the surface that is in contact with the patient's skin 302.

One definition of 'flexible' is "capable of bending easily without breaking." The term 'flexible' is applied to various degrees of this capability to bend without breaking. Items that are sometimes described as 'flexible' include a thin sheet of rubber, which can be folded tightly upon itself without breaking, and a thin cantilevered steel rod, which will bend a perceptible amount when a transverse load is applied at its tip and return to its original position when the load is removed. In the context of the disclosed vital-signs monitor patch 20, the segments 310 of the patch 20 that are considered flexible are able to be bent by hand with very little effort into shapes that have one or more curves. The flexible patch segments 310 need not be bendable into sharp corners or folded flat against themselves. In the configuration where a compressive force is applied in the plane of the flexible segment 310 of the patch 20, the segment 310 will assume a wavy shape that is shorter in the direction of the applied force than prior to the application of the force, and the amount of force required to compress the segment 310 a small amount, on the order of a few percent, is negligible. Thus, application of term 'flexible' to a segment 310 of the patch 20 that has an electrode 320 attached at one end implies an ability of the patch segment 310 to assume a shape with a reduced length with the load applied by the electrode 320 below the level that would create noise artifacts.

It has been observed that the quality of the electrical connection of electrodes to a patient's body is strongly affected by mechanical stress on the connection between the electrode and the skin. This shows up as noise artifacts in the measurement signal as the impedance of the connection changes with stress on the connection. For example, the skin across the chest contracts as a patient reaches forward with both hands. When this happens, a pair of rigidly connected electrodes that were adhered to the chest of a patient while the patient's hands were at their sides will experience significant shear force on each connector when the patient reaches forward with both hands. The noise artifacts induced in this situation in the signal from these electrodes are referred to as "motion induced noise." Even something as minor as sitting up or walking around, both of which involve simple arm motions, are enough to produce significant noise in the measurement of respiration or pulse.

Figure 3C:
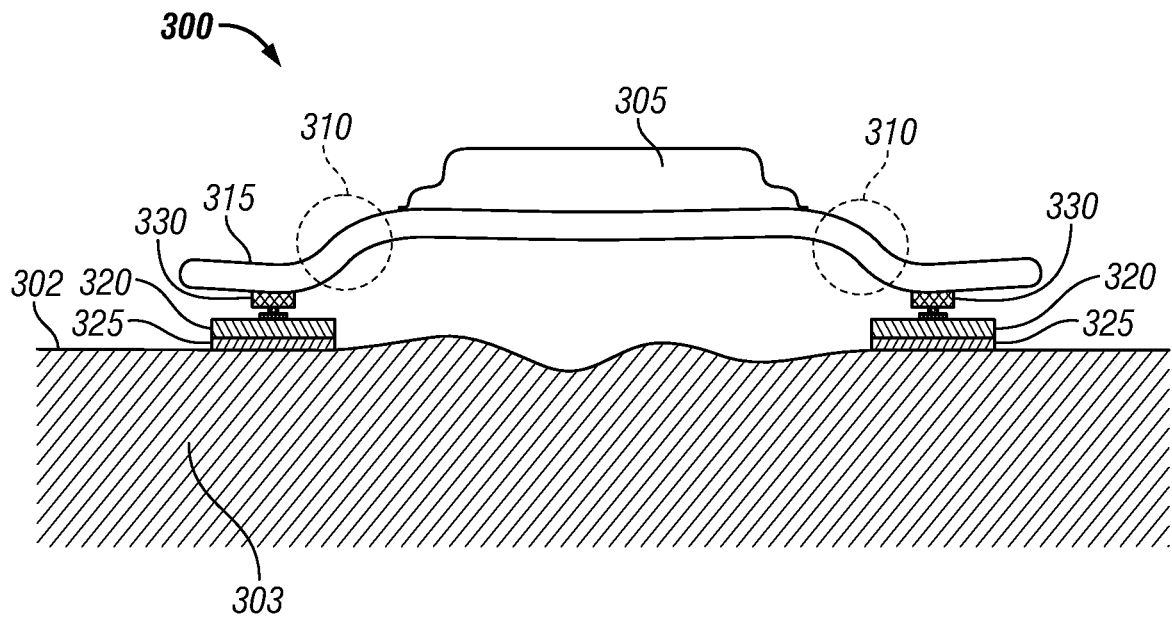
Figure 3D:
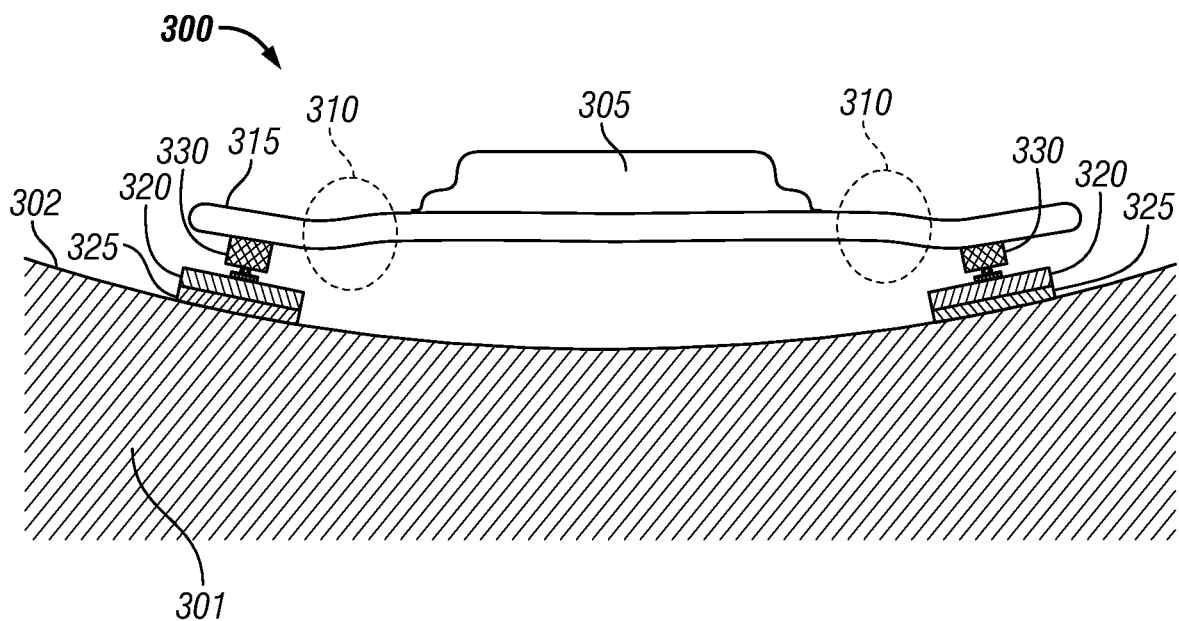

FIGS. 3C and 3D show displaced configurations of patch 300 when the patient 10 bends or moves such that the portion of the patient's body 301 under patch 300 is no longer of the same shape as it was when the patch was initially applied, as would be typified by the configuration of FIG. 3B. In FIG. 3C, the patient is pulling on something such that the chest muscles 303 are contracting and the distance between the adhered electrodes 320 is reduced. As the electrodes 320 move towards each other, the flexible segments 310 will bend and deform to accommodate this motion. As a result, there is very little shear stress placed on the adhesive 325 of electrodes 320. FIG. 3D shows a similar configuration where the patient 330 has bent over or moved such that the area under the patch 300 is now curved. The flexible segments 310 have changed shape to accommodate the motion and avoid applying stress to the adhesive 325 of electrodes 320. In addition, the swivel capability of connectors 330 permits rotary motion of the patch flaps 315 relative to the electrodes 320 and avoided tension and compression stresses on the adhesive 325.

The disclosed embodiments of patch 300 provide a significant reduction in noise in the measurements of vital signs as the patient moves about during normal activities. As an advantage of a vital-signs monitor 20 is its continuous monitoring during normal activity, reduced motion-induced noise artifacts enables electrodes 320 to be closer together, which further enables the entire patch 20 to be smaller and less intrusive in the patient's activities.

Figure 4A:
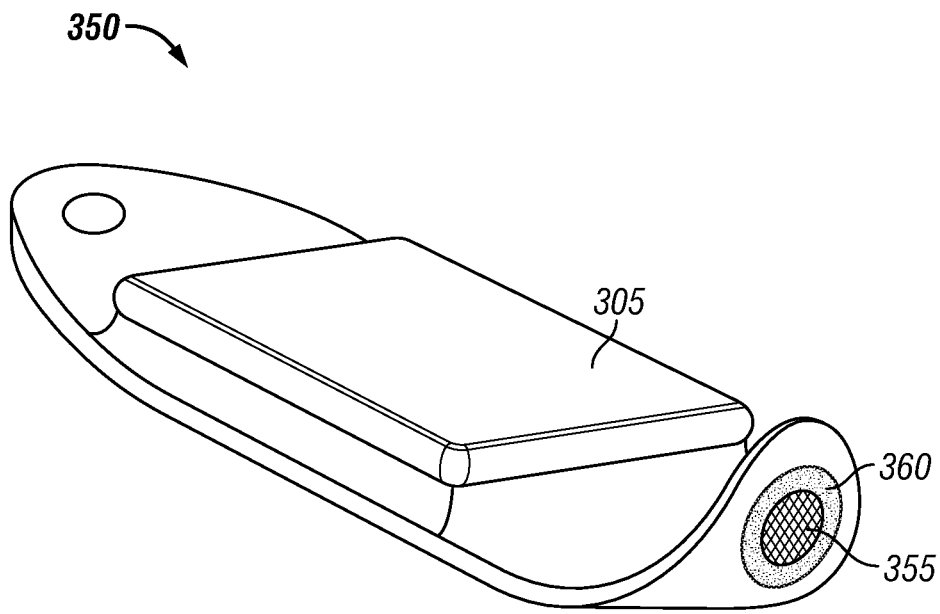
FIG. 4A is a perspective view of another embodiment of a patient monitoring system according to certain aspects of the present disclosure.
Figure 4B:
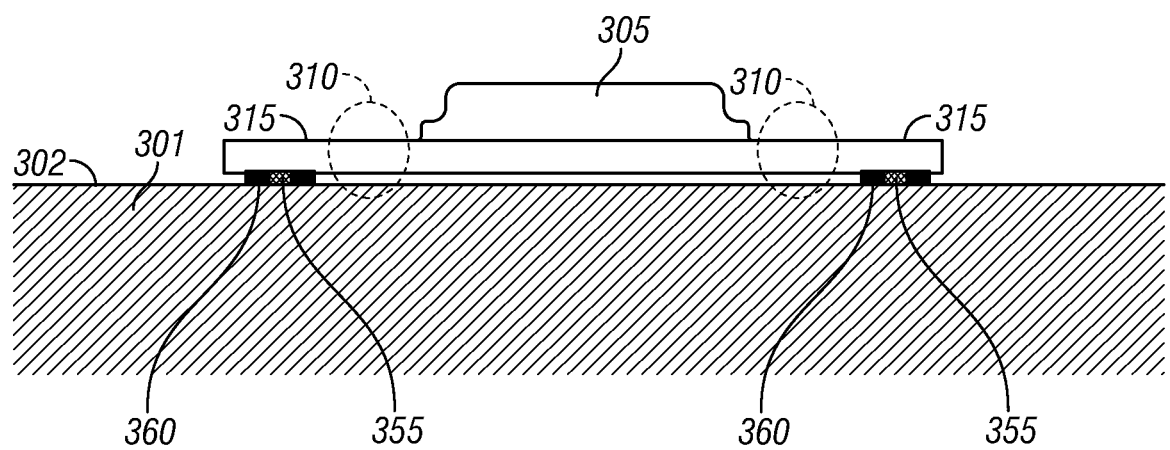
FIGS. 4B, 4C, and 4D are side views of the embodiment of FIG. 4A in various displaced configurations.
Figure 4C:
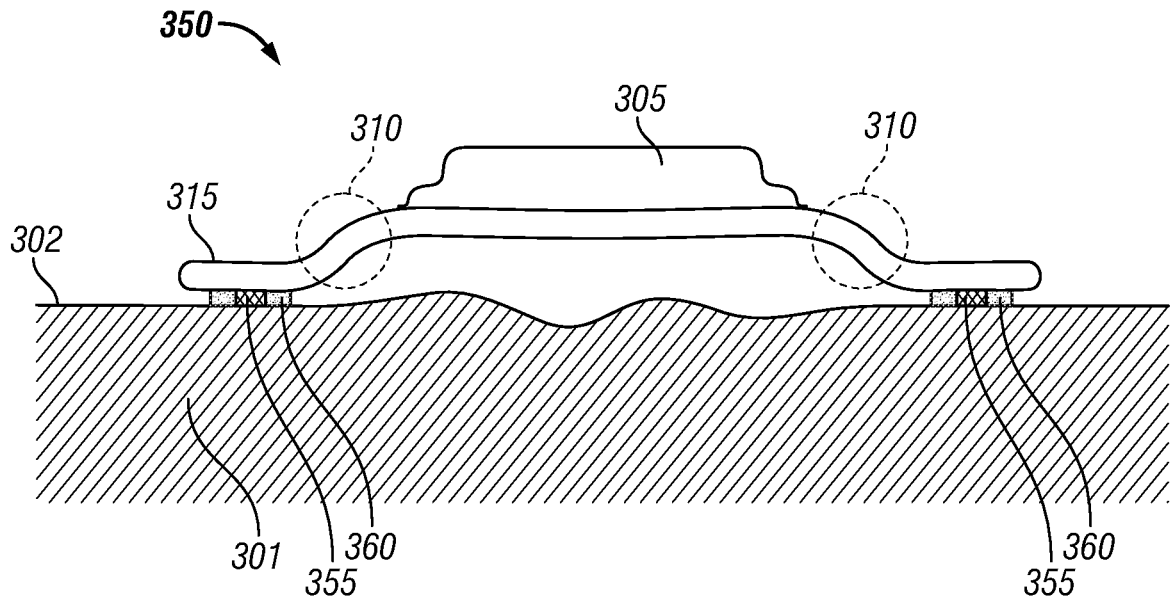
Figure 4D:
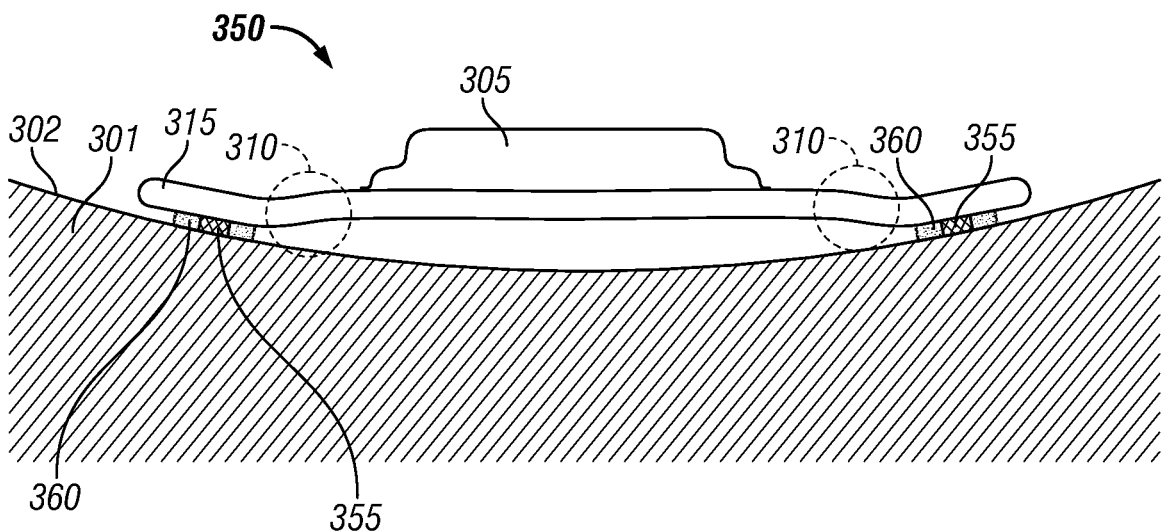

The flexible connection between the electrodes 320 and the circuit assembly package 305 can be accomplished in a variety of configurations without departing from the scope of the present disclosure. FIG. 4A shows an alternate embodiment of patch 350, wherein the electrodes 355 are configured such that the surface of the electrode 355 is approximately flush with the surface of the patch body. This could be implemented as either a coating or film applied to the surface of the patch body or an electrode embedded in the material of the body. In this embodiment, conductive adhesive 360 is applied around electrode 355 allowing a conductive gel (not shown) to be utilized between electrode 355 and the skin 302 to improve electrical contact. The patch 20 has flexible segments 310 between the central section 305 and the electrodes 355. FIGS. 4C and 4D illustrate the behavior of the flexible segments 310 in accommodating movement of the patient 10 without inducing stress in the adhesive 360 of the path so as to avoid inducing noise artifacts in the signal.

Figure 5A:
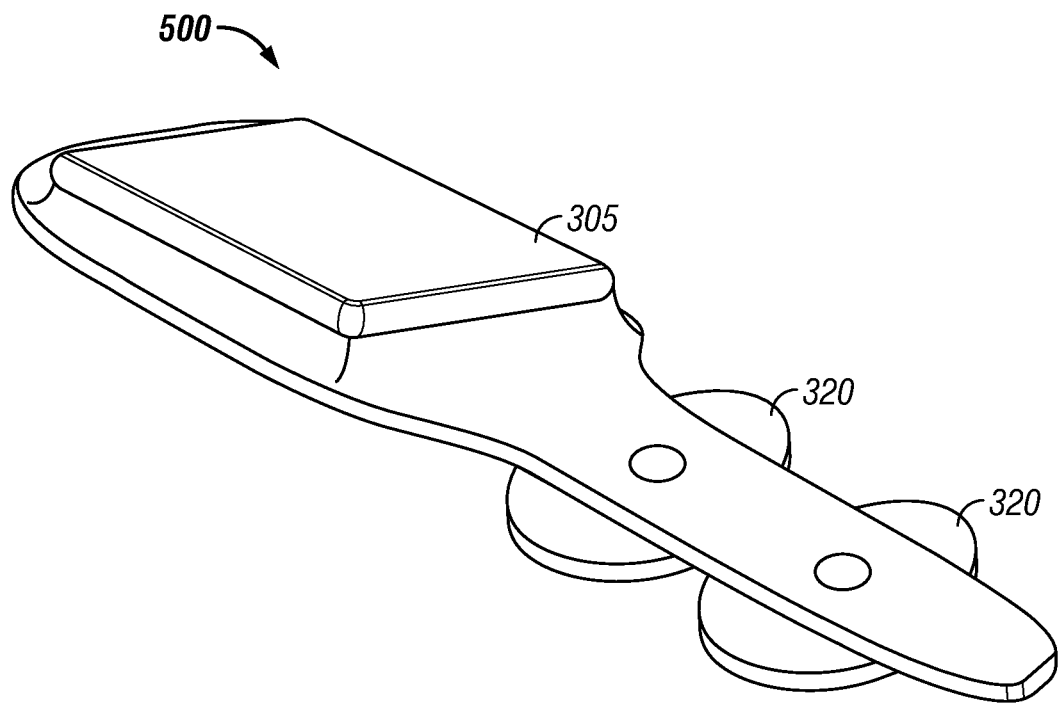
FIGS. 5A and 5B are perspective views of additional embodiments of a patient monitoring system according to certain aspects of the present disclosure.
Figure 5B:
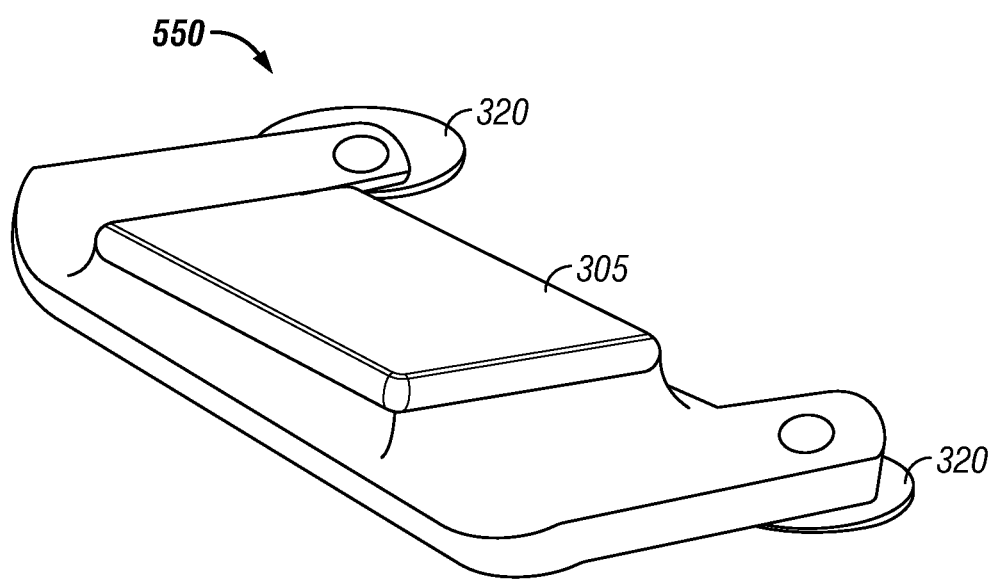

FIGS. 5A and 5B illustrate additional configurations of a vital-signs patch that are within the scope of the claims. Patch 500 of FIG. 5A shows the two electrodes 320 positioned on a common side of central section 305. Adhesive (not shown) may be applied to the underside of central section 305 to provide mechanical attachment to the patient. FIG. 5B shows patch 550 where the electrodes 320 are on opposite sides of central section 305 in one direction and on a common side of central section 305 in the perpendicular direction. Patch 500 and 550 may be suitable for use in specific care situations or in conjunction with certain medical procedures.

It can be seen that the disclosed embodiments of the vital-signs monitor patch provide a mobile solution to monitoring the vital signs of a patient. The design of the vital-signs monitor patch frees nurses, or other caregivers, from the task of repetitively measuring the vital signs of their patients, allowing the caregivers to spend more time on other duties. The ability to continuously monitor a patient's vital signs using a monitor patch, together with the rest of the patient monitoring system, increases the ability of the nurse to respond quickly to a sudden change in a patient's condition, resulting in improved care for the patient.

The strain relief capability of the patch body in the area between the electrodes reduces the magnitude of noise-induced noise artifacts in the measurement signals taken by the vital-signs monitoring patch. As noise is one of the limiting factors in reducing the size of the monitor patch, a lower level of noise enables the patch to be smaller. A smaller patch is less intrusive to the patient and easier for the nurse or other caregiver to apply.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A vital-signs monitor patch, comprising:
   a rigid portion that includes a circuit assembly configured to receive and process vital-signs monitoring signals of a single patient from first and second electrodes attached to skin of the patient;
   first and second flexible portions extending from opposing sides of the rigid portion along a central axis, the first and second flexible portions each comprising an extension that extends perpendicularly from the central axis in the same direction and in parallel to one another;
   a patient facing surface formed by an outer patient facing surface of each of the rigid portion and the flexible portion;
   a first snap fitting disposed adjacent to the outer patient facing surface of the flexible portion, the first snap fitting configured to be disposed between the flexible portion and the skin of the patient and to rotatably attach to the first electrode; and
   a second snap fitting disposed adjacent to the outer patient facing surface of the flexible portion, the second snap fitting configured to be disposed between the flexible portion and the skin of the patient and to rotatably attach to the second electrode,
   wherein the first and second flexible portions are configured to allow the rigid portion to be movable with respect to the skin of the patient when the first and second snap fittings are connected to the first and second electrodes and the first and second electrodes are attached to the skin of the patient,
   wherein the first and second electrodes are disposed respectively on the extensions of the first and second flexible portions, and
   wherein the rigid portion and the first and second flexible portions, including the extensions, are oriented in a common plane when the vital-signs monitor patch is not in use.

2. The vital-signs monitor patch of claim 1, wherein each electrode comprises a layer of adhesive that is configured to attach the electrode to the patient's skin.

3. The vital-signs monitor patch of claim 1, wherein a first portion of the first snap fitting is configured to rotatably attach to a second portion of the first snap fitting, the second portion of the first snap fitting disposed on the first electrode.

4. The vital-signs monitor patch of claim 3, wherein a first portion of the second snap fitting is configured to rotatably attach to a second portion of the second snap fitting, the second portion of the second snap fitting disposed on the second electrode.

5. The vital-signs monitor patch of claim 1, wherein the vital-signs monitoring signals correspond to at least one of a temperature, a pulse rate, a respiration rate, a blood pressure or an oxygen saturation.

6. The vital-signs monitor patch of claim 1, wherein the circuit assembly comprises a printed circuit board.

7. The vital-signs monitor patch of claim 6, wherein the circuit assembly further comprises an internal sensor configured to measure a temperature of the printed circuit board.

8. A system comprising:
   a plurality of vital-signs monitor patches, each patch comprising:
      a rigid central portion that includes a circuit assembly configured to receive and process vital-signs monitoring signals of a single patient from first and second corresponding electrodes attached to skin of the single patient;
      first and second flexible portions each extending from opposite sides of the central portion along a longitudinal axis;

a patient facing surface formed by an outer patient facing surface of each of the central portion, the first flexible portion and the second flexible portion;

a first snap fitting disposed adjacent to the outer patient facing surface of an extended portion of the first flexible portion, the first snap fitting configured to be disposed between the first flexible portion and the first corresponding electrode and to rotatably attach to the first corresponding electrode, a second snap fitting disposed adjacent to the outer patient facing surface of an extended portion of the second flexible portion parallel to the extended portion of the first flexible portion, the second snap fitting configured to be disposed between the second flexible portion and the second corresponding electrode and to rotatably attach to the second corresponding electrode, wherein the first and second flexible portions are configured to allow the rigid central portion to be movable with respect to the skin of the corresponding patient when the first and second snap fittings are connected to the first and second corresponding electrodes disposed on the parallel extended portions of the first and second flexible portions respectively, and the first and second corresponding electrodes are attached to the skin of the corresponding patient, wherein the first and second electrodes are disposed on opposing sides of the central portion along the longitudinal axis and are disposed on a same side of the central portion in a same direction perpendicular to the longitudinal axis, wherein the first flexible portion, the extended portion of the first flexible portion, the rigid central portion, the second flexible portion and the extended portion of the second flexible portion are all oriented along a common plane when the vital-signs monitor patch is not in use; and a server configured to receive and process measurement signals from the circuit assembly of each of the patches for each corresponding patient.

9. The system of claim 8, wherein the server is further configured to send a message to a mobile device if one or more of the measurement signals exceeds specified parameters.

10. The system of claim 9, further comprises a bridge configured to facilitate wireless communications between at least one of the patches and the server.

11. The system of claim 10, wherein the bridge is configured to facilitate the wireless communications by performing data buffering and protocol conversion that enables bidirectional signal transmission between the at least one of the patches and the server.

12. The system of claim 8, wherein, for each patch, a first portion of the first snap fitting is configured to rotatably attach to a second portion of the first snap fitting, the second portion of the first snap fitting disposed on the first corresponding electrode.

13. The system of claim 12, wherein a first portion of the second snap fitting is configured to rotatably attach to a second portion of the second snap fitting, the second portion of the second snap fitting disposed on the second corresponding electrode.

14. The system of claim 8, wherein the vital-signs monitoring signals correspond to at least one of a temperature, a pulse rate, a respiration rate, a blood pressure or an oxygen saturation for the corresponding patient.

15. A vital-signs monitor patch, comprising:
a rigid central portion;
a circuit assembly disposed in the rigid central portion, wherein the circuit assembly is configured to receive and process vital-signs monitoring signals of a single patient from first and second electrodes;

a first flexible portion extending laterally from a first side of the central portion along a longitudinal axis, wherein an extended portion of the first flexible portion extends away from the longitudinal axis in a first direction along a first orthogonal axis perpendicular to the longitudinal axis;

a second flexible portion extending laterally from a second side of the central portion opposite the first side of the central portion along the longitudinal axis, wherein an extended portion of the second flexible portion extends away from the longitudinal axis in the first direction along a second orthogonal axis perpendicular to the longitudinal axis, wherein the first orthogonal axis is parallel to the second orthogonal axis, and wherein the first flexible portion, the rigid central portion and the second flexible portion are oriented along a common plane when the vital-signs monitor patch is not in use;

a patient facing surface formed by an outer patient facing surface of each of the central portion, the first flexible portion and the second flexible portion;

a first snap fitting disposed adjacent to the outer patient facing surface on the extended portion of the first flexible portion, the first snap fitting configured to be disposed between the first flexible portion and the first electrode; and a second snap fitting disposed adjacent to the outer patient facing surface on the extended portion of the second flexible portion, the second snap fitting configured to be disposed between the second flexible portion and the second electrode, wherein the first snap fitting is configured to rotatably attach to the first electrode, wherein the second snap fitting is configured to rotatably attach to the second electrode, wherein the first and second flexible portions are configured to allow the rigid central portion to move relative to the first and second snap fittings, and wherein the first and second electrodes are disposed on opposite sides of the central portion along the longitudinal axis and on a same side of the central portion in the common plane.

16. The vital-signs monitor patch of claim 15, wherein the first snap fitting is configured to rotatably attach to a complementary snap feature on the first electrode.

17. The vital-signs monitor patch of claim 16, wherein the second snap fitting is configured to rotatably attach to a complementary snap feature on the second electrode.

18. The vital-signs monitor patch of claim 15, wherein the vital-signs monitoring signals correspond to at least one of a temperature, a pulse rate, a respiration rate, a blood pressure or an oxygen saturation.

19. The vital-signs monitor patch of claim 15, wherein the circuit assembly comprises a printed circuit board.

20. The vital-signs monitor patch of claim 19, wherein the circuit assembly further comprises an internal sensor on the printed circuit board and configured to monitor the circuit assembly.

* * * * *